United States Patent [19]
Chen et al.

[11] Patent Number: 6,013,239
[45] Date of Patent: Jan. 11, 2000

[54] LARGE CRYSTAL ZSM-5, ITS SYNTHESIS AND USE

[75] Inventors: Catherine Shuihua Hsia Chen, Berkeley Heights; Frank Thomas Diguiseppi, Bordentown, both of N.J.; Thomas Reginald Forbus, Jr., Newtown; Mae Koenig Rubin, Bala Cynwyd, both of Pa.; Sanjay Bhardwaj Sharma, Burr Ridge, Ill.; David Said Shihabi, Pennington, N.J.; Hye Kyung Cho Timken, Woodbury, N.J.; Steven Edward Wentzek, Edison, N.J.

[73] Assignee: Mobil Oil Corporation, Fairfax, Va.

[21] Appl. No.: 08/952,030

[22] PCT Filed: Jun. 6, 1996

[86] PCT No.: PCT/US96/09878

§ 371 Date: Nov. 4, 1997

§ 102(e) Date: Nov. 4, 1997

[87] PCT Pub. No.: WO96/40426

PCT Pub. Date: Dec. 19, 1996

Related U.S. Application Data

[63] Continuation-in-part of application No. 08/469,181, Jun. 6, 1995, abandoned.

[51] Int. Cl.[7] .................................................. C01B 39/40
[52] U.S. Cl. .................... 423/705; 423/705; 423/706; 423/708; 423/716; 423/DIG. 22
[58] Field of Search ................................. 423/701, 702, 423/704, 705, 706, 708, 713, 714, 715, 716, DIG. 22; 502/77

[56] References Cited

U.S. PATENT DOCUMENTS

| | | |
|---|---|---|
| 4,088,605 | 5/1978 | Rollmann ........................ 423/DIG. 22 |
| 4,203,869 | 5/1980 | Rollmann . |
| 4,331,641 | 5/1982 | Hinnenkamp et al. . |
| 4,650,656 | 3/1987 | Dwyer et al. . |
| 5,365,002 | 11/1994 | Wallau et al. .................... 423/DIG. 22 |
| 5,573,746 | 11/1996 | Chen ....................................... 423/706 |

FOREIGN PATENT DOCUMENTS

| | | |
|---|---|---|
| 3 239 054 | 10/1982 | Germany . |
| 1611783 | 7/1990 | Japan . |
| 2 023 562 | 6/1979 | United Kingdom . |

OTHER PUBLICATIONS

"Concerning the Aluminum Distribution Gradient in ZSM–5 Zeolites", Derouane et al., Journal of Catalysis, 1981, vol 71, pp. 447–8 (No Month).

*Primary Examiner*—Mark L. Bell
*Assistant Examiner*—David Sample
*Attorney, Agent, or Firm*—Peter W. Roberts; Malcolm D. Keen

[57] ABSTRACT

In a synthetic porous crystalline material having the structure of ZSM-5 and a composition involving the molar relationship: $X_2O_3:(n)YO_2$, wherein X is a trivalent element; Y is a tetravalent element; and n is greater than about 12, the crystals have a major dimension of at least about 0.5 micron and surface framework $YO_2/X_2O_3$ ratio which is no more than 20% less than the bulk framework $YO_2/X_2O_3$ ratio of the crystal. The material is synthesized using an amino-acid as a directing agent.

10 Claims, 7 Drawing Sheets

LARGE CRYSTAL ZSM-5, ITS SYNTHESIS AND USE

This application is a continuation-in-part of U.S. application Ser. No. 08/469181, filed Jun. 6, 1995, now abandoned.

This invention relates to large crystal ZSM-5, its synthesis and its use in catalytic processes.

BACKGROUND OF THE INVENTION

ZSM-5 and its synthesis using tetrapropylammonium (TPA) cations as a directing agent are disclosed in U.S. Pat. No. 3,702,886. EP-A-21674 teaches that large crystal ZSM-5, having a crystal size in excess of 1 micron, can be prepared from a reaction mixture containing TPA cations provided the OH–/$SiO_2$ ratio is maintained within the range 0.01–0.07.

Large crystal ZSM-5 (>0.5 micron) usually can be prepared without difficulty when the aluminum content in the synthesis mixture is low. As a result, with large crystal ZSM-5, although $SiO_2/Al_2O_3$ ratios of 100 or higher are relatively easily attainable, $SiO_2/Al_2O_3$ ratios of 40 or lower are difficult to attain.

In conventionally prepared, large ZSM-5 crystals, the aluminum distribution tends to be non-uniform with a significantly higher aluminum concentration (>20%) being found on the outer surface, as compared with the interior, of the crystal. Aluminum zoning in ZSM-5, especially in large crystals, has been reported. See "Zoned Aluminum Distribution in Synthetic Zeolite ZSM-5", R. von Ballmoos & W. M. Meier, Nature 1981, 289, 782–3; "Aluminum Distribution in Large ZSM-5 Crystals", K. J. Chao & J. Y. Chern, Zeolites, 1988, 8, 82; "Aluminum Zoning in ZSM-5 As Revealed by Selective Silica Removal", R. M. Dessau, E. W. Valyocsik & N. H. Goeke, Zeolites, 1992, 12, 776.

SUMMARY OF THE INVENTION

Unexpectedly it has now been found that by using amino acids as the directing agent, large crystal ZSM-5 of high aluminum content, $SiO_2/Al_2O_3$=25–40, can readily be obtained. Moreover, the resultant large ZSM-5 crystals have essentially the same $SiO_2/Al_2O_3$ ratios in bulk (as measured by elemental and NMR analyses) and on the surface (as measured by x-ray photoelectron spectroscopy analysis (XPS) which determines the surface concentration and oxidation state of all detectable elements.)

It is to be appreciated that, although ZSM-5 is normally synthesized as an aluminosilicate, the framework aluminum can be partially or completely replaced by other trivalent elements, such as boron, iron and/or gallium, and the framework silicon can be partially or completely replaced by other tetravalent elements such as germanium.

In one aspect, the invention resides in a synthetic porous crystalline material having the structure of ZSM-5 and a composition involving the molar relationship:

$$X_2O_3:(n)YO_2,$$

wherein X is a trivalent element, such as aluminum, boron, iron and/or gallium, preferably aluminum; Y is a tetravalent element such as silicon and/or germanium, preferably silicon; and n is greater than about 12, and wherein the crystals have a major dimension of at least about 0.5 micron and a surface framework $YO_2/X_2O_3$ ratio which is no more than 20% less than the bulk framework $YO_2/X_2O_3$ ratio of the crystal.

Preferably, the crystals have a major dimension of at least about 1 micron.

Preferably, the surface framework $YO_2/X_2O_3$ ratio is no more than 10% less than the bulk framework $YO_2/X_2O_3$ ratio of the crystal.

Preferably, n is less than about 100 and more preferably is about 25 to about 40.

Preferably, the crystalline material exhibits a sorption time for 2,2-dimethylbutane for 30% of its capacity, as measured at 120° C. and 60 torr (8 kPa) hydrocarbon pressure, of at least 5 minutes, preferably at least 10 minutes.

In a further aspect, the invention resides in a synthetic porous crystalline material having the structure of ZSM-5 and a Toluene Disproportionation Index (as hereinafter defined) of less than 430, and preferably less than 400.

In yet a further aspect, the invention resides in a method of synthesizing said porous crystalline material having the structure of ZSM-5 comprising the steps of forming a reaction mixture containing sources of an alkali or alkaline-earth metal oxide, a trivalent metal oxide $X_2O_3$, a tetravalent metal oxide $YO_2$, water, and an amino acid or salt thereof having the formula:

wherein $R_1$ is $NH_2$, $NHR_3$ where $R_3$ is an adamantyl or cyclic alkyl group, or a carboxylic acid group or salt thereof; $R_2$ is H, alkyl, aryl, alkaryl, $NH_2$ or $NHR_3$ where $R_3$ is an adamantyl or cyclic alkyl group; provided that at least one of $R_1$ and $R_2$ is $NH_2$ or $NHR_3$, A is H or a metal and z is from 0 to 15, provided that at least one of $R_1$ and $R_2$ is $NH_2$ or $NHR_3$, and crystallizing the reaction mixture to produce said porous crystalline material.

Preferably, the amino acid or salt thereof is selected from 6-aminohexanoic acid, lysine, glutamic acid and monosodium glutamate.

BRIEF DESCRIPTION OF THE DRAWINGS

The invention will now be more particularly described with reference to the accompanying drawings, in which.

DESCRIPTION OF THE INVENTION

The present invention provides a novel form of large crystal ZSM-5 having a composition involving the molar relationship:

$$X_2O_3:(n)YO_2,$$

wherein X is a trivalent element, such as aluminum, boron, iron and/or gallium, preferably aluminum; Y is a tetravalent element such as silicon and/or germanium, preferably silicon; and n is greater than about 12, preferably less than 100 and most preferably 25–40, and wherein the crystals have a surface framework $YO_2/X_2O_3$ ratio which is no more than 20% less, and preferably no more than 10% less, than the bulk framework $YO_2/X_2O_3$ ratio of the crystal.

The term "large crystal" ZSM-5 is used herein to mean that the crystals have a major dimension, and preferably at least two dimensions, of at least about 0.5 micron, preferably at least 1 micron and most preferably about 1 to about 10 microns as measured by standard SEM techniques. The crystal size of ZSM-5 can also be deduced from sorption measurements, for example by measuring the rate of sorption of 2,2-dimethylbutane at 120° C. and 60 torr (8 kPa) hydrocarbon pressure. The crystal size is computed by applying the diffusion equation given by J. Crank, *The Mathematics of Diffusion*, Clarendon-Press, 52–56 (1957), for the rate of sorbate uptake by a solid whose diffusion properties can be approximated by a plane sheet model. In addition, the diffusion constant of 2,2-dimethylbutane, D, under these conditions, is taken to be $1.5 \times 10^{-14}$ cm$^2$/sec. The relation between crystal size measured in microns, d, and diffusion time measured in minutes, $t_{0.3}$, the time required for the uptake of 30% capacity of hydrocarbon, is:

$$d = 0.0704 \times t_{0.3}^{1/2}$$

The large crystal ZSM-5 according to the invention preferably has a sorption time, $t_{0.3}$, of at least 5 minutes, and preferably at least 10 minutes.

The novel ZSM-5 of the invention is characterized by a unique behavior when silicon-selectivated for use in the para-selective disproportionation of toluene. This unique behavior is reflected in the Toluene Disproportionation Index of the zeolite which is less than 430 and preferably less than 400. The Toluene Disproportionation Index is a convenient measure of the para-selectivity and toluene conversion activity of the zeolite, both of which properties are vital to the successful operation of a catalyst for converting toluene to para-xylene. The Toluene Disproportionation Index is measured by passing a 2 wt % solution of hexamethyldisiloxane in toluene over a sample of the unbound zeolite in the hydrogen form at a temperature of 446° C., a pressure of 300 psig (2170 kPa), a WHSV of 3 and in the presence of hydrogen to provide a $H_2$/toluene molar ratio of 2:1. A siliceous deposit is thereby produced on the zeolite which increases the selectivity of the zeolite for the conversion of the toluene to para-xylene. The reaction products are sampled at regular intervals and analyzed by gas chromatography and, when the para-xylene selectivity reaches 90% by weight of the total $C_8$ component, the hexamethyldisiloxane/toluene feed is changed to pure toluene and the temperature adjusted to produce a toluene conversion level of 30 wt %. The reaction temperature (°C.) at which the the p-xylene selectivity is 90 wt % and the toluene conversion is 30 wt % is the defined as the Toluene Disproportionation Index (TDI).

The novel large crystal ZSM-5 of the invention is produced from a reaction containing sources of an alkali or alkaline-earth metal (M) oxide, a trivalent metal oxide $X_2O_3$, a tetravalent metal oxide $YO_2$, water, and an amino acid or salt thereof (AA) having the formula:

wherein $R_1$ is $NH_2$, $NHR_3$ where $R_3$ is an adamantane or cyclic alkyl group, or is a carboxylic acid group or salt thereof; $R_2$ is H, alkyl, aryl, alkaryl, $NH_2$ or $NHR_3$ where $R_3$ is an adamantane or cyclic alkyl group; A is H or a metal and z is from 0 to 15, preferably 1–7; provided that at least one of $R_1$ and $R_2$ is $NH_2$ or $NHR_3$. Examples of suitable amino acids are 6-aminohexanoic acid, N-2-adamantylglycine, N-cyclohexylglycine, lysine, and glutamic acid (and its monosodium salt).

The reaction mixture has a composition, expressed in terms of mole ratios of oxides, as follows:

|  | Useful | Preferred |
|---|---|---|
| $YO_2/X_2O_3$ | 20–80 | 20–40 |
| $H_2O/YO_2$ | 10–90 | 20–60 |
| $AA/YO_2$ | 0.05–0.5 | 0.1–0.2 |
| $M/YO_2$ | 0.1–0.8 | 0.3–0.4 |

The synthesis method of the invention functions with or without added nucleating seeds. In a preferred embodiment, the reaction mixture contains no nucleating seeds. The preferred aluminum source is $NaAlO_2$, while the preferred silicon source is $SiO_2$ sol (30% $SiO_2$ in $H_2O$), which is commercially available as Catalog No. SX0140-1 from EM Science, Inc.

Crystallization is carried out under either stirred or static conditions at a temperature of 80 to 225° C., preferably 120 to 200° C., for 24 hours to 60 days and the resultant ZSM-5 crystals are separated from the mother liquor and recovered.

Since the large crystal ZSM-5 of the invention can be synthesized with a relatively low silica/alumina molar ratio (that is with a relatively high aluminum content), the invention can be used to produce large crystal ZSM-5 with a high catalytic activity. Catalytic activity of zeolites, such as ZSM-5, is typically measured by Alpha Value, which compares the catalytic cracking activity of the catalyst (rate of normal hexane conversion per volume of catalyst per unit time) with the activity of a standard silica-alumina cracking catalyst. The Alpha Test is described in U.S. Pat. No. 3,354,078; in the *Journal of Catalysis*, Vol. 4, p. 527 (1965); Vol. 6, p. 278 (1966); and Vol. 61, p. 395 (1980). The experimental conditions of the test used herein include a constant temperature of 538EC and a variable flow rate as described in detail in the *Journal of Catalysis*, Vol. 61, p. 395. In the hydrogen form, the large crystal ZSM-5 of the invention preferably has an Alpha Value in excess of 300 and preferably in excess of 800.

When used as a catalyst, it may be desirable to incorporate ZSM-5 of the invention with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the ZSM-5 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided ZSM-5 material and inorganic oxide matrix vary widely, with the ZSM-5 content ranging from about 1 to about 90% by weight and more usually, particularly when the composite is prepared in the form of beads, in the range of about 2 to about 80 wt. % of the composite.

The large crystal ZSM-5 of the invention is useful as a catalyst for aromatics alkylation and transalkylation processes, such as toluene disproportionation, and other shape-selective processes which typically use ZSM-5 or other medium pore zeolites as catalysts.

In order to more fully illustrate the nature of the invention and the manner of practicing same, the following examples are presented.

EXAMPLE 1

Synthesis of N-2-adamantylglycine

A 600 ml stainless steel Parr reactor, equipped with a stirrer, two inlets, one with a tubing reaching nearly to the bottom of the reactor, and an outlet was used. Into the open reactor there were charged 100 grams of glycine (Aldrich, 99+%), 206.7 grams of 2-adamantanone (Aldrich, 99%), 10 grams of palladium (5%) on charcoal, and 300 grams of glacial acetic acid. The reactor was closed and dry nitrogen was passed through said one inlet into the reaction mixture to replace the air in the reaction mixture and in the reactor. The nitrogen was turned off and the reactor was pressurized with hydrogen through the other inlet. Under a hydrogen pressure of 725 psig (5100 kPa), the reaction mixture was heated to 100° C. and stirred at this temperature for 5 days. After cooling down to room temperature, the excess hydrogen was vented from the reactor and the reactor was opened. The mixture was filtered by suction to remove the solid Pd/C catalyst. The filtrate was evaporated to remove the acetic acid and water. The crude product was washed with ether and recrystallized from a dilute aqueous solution. A pure product was obtained after two recrystallization. Elemental analysis:Calculated for $C_{12}H_{17}NO_2$:C:68.67; H:9.15; N:6.69. Found C:68.85; H:9.12; N:6.75. M.P.:255.4 C (by DSC at 10 C/min. under He).

EXAMPLE 2

ZSM-5 synthesis using N-2-adamantylglycine

A stock solution of NaOH and $NaAlO_2$ in deionized $H_2O$ was prepared by dissolving 16.26 grams (0.198 moles) anhydrous $NaAlO_2$, 43.55 grams NaOH (1.09 moles) in 2925 grams (162.5 moles) $H_2O$. To 268.8 grams of the $NaAlO_2$/NaOH stock solution were added 6.1 grams (0.029 moles) N- 2-damantylglycine. The template was not readily soluble at room temperature but a clear solution was formed upon heating to 75° C. To this clear solution was added 58.1 grams $SiO_2$ sol (30% or 17.4 grams or 0.29 moles $SiO_2$) with vigorous stirring and a gel was formed. The gel had the following molar composition:

$SiO_2/Al_2O_3$=32.5

$Al_2O_3/Na_2O$=0.18

$H_2O/SiO_2$=50

$Na+/SiO_2$=0.4

$OH-/SiO_2$=0.34

Directing agent/$SiO_2$=0.1

Figure 1:
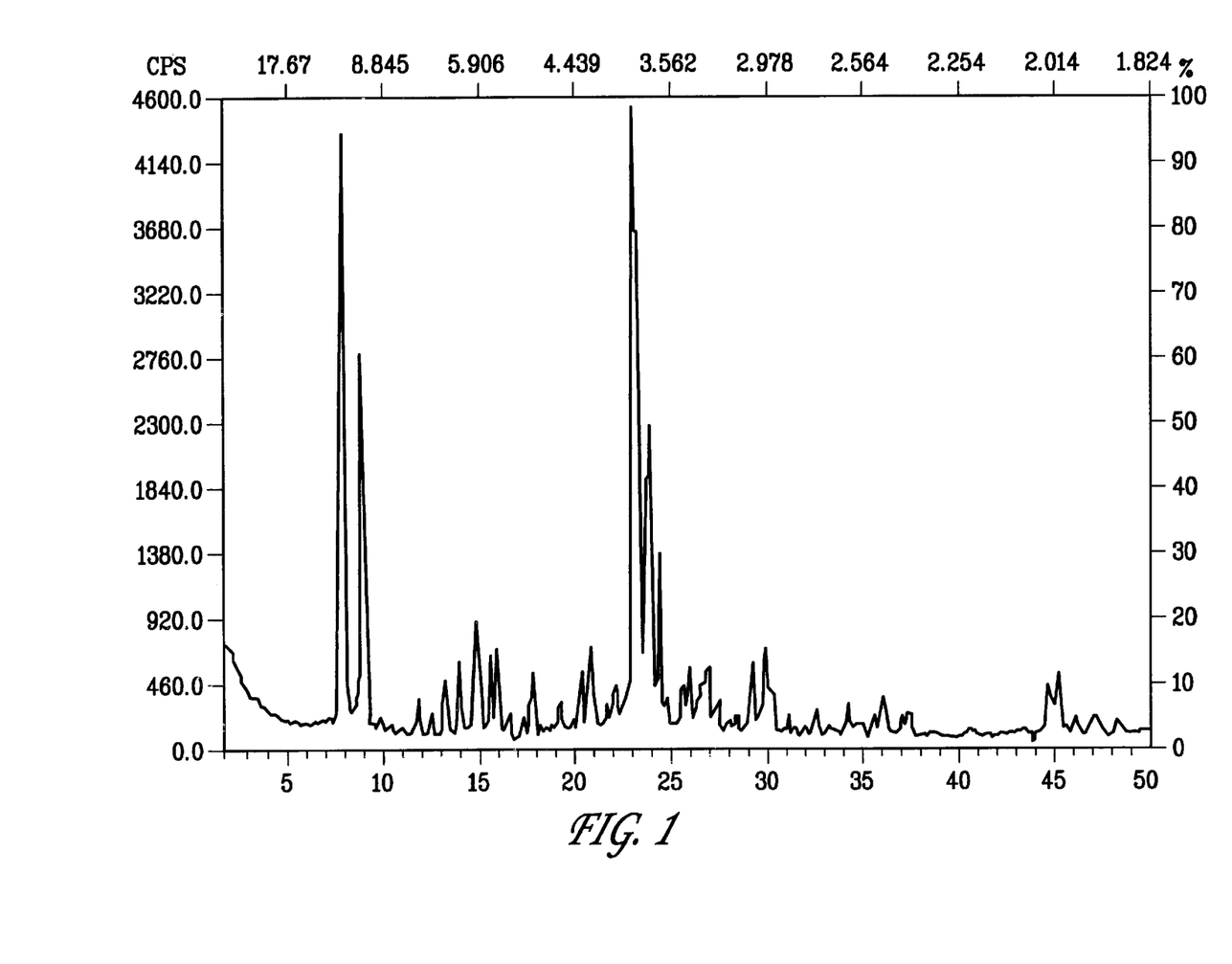
FIG. 1 is an x-ray diffraction pattern of the calcined ZSM-5 produced using N-2-adamantylglycine as the directing agent (Example 2).
Figure 2:
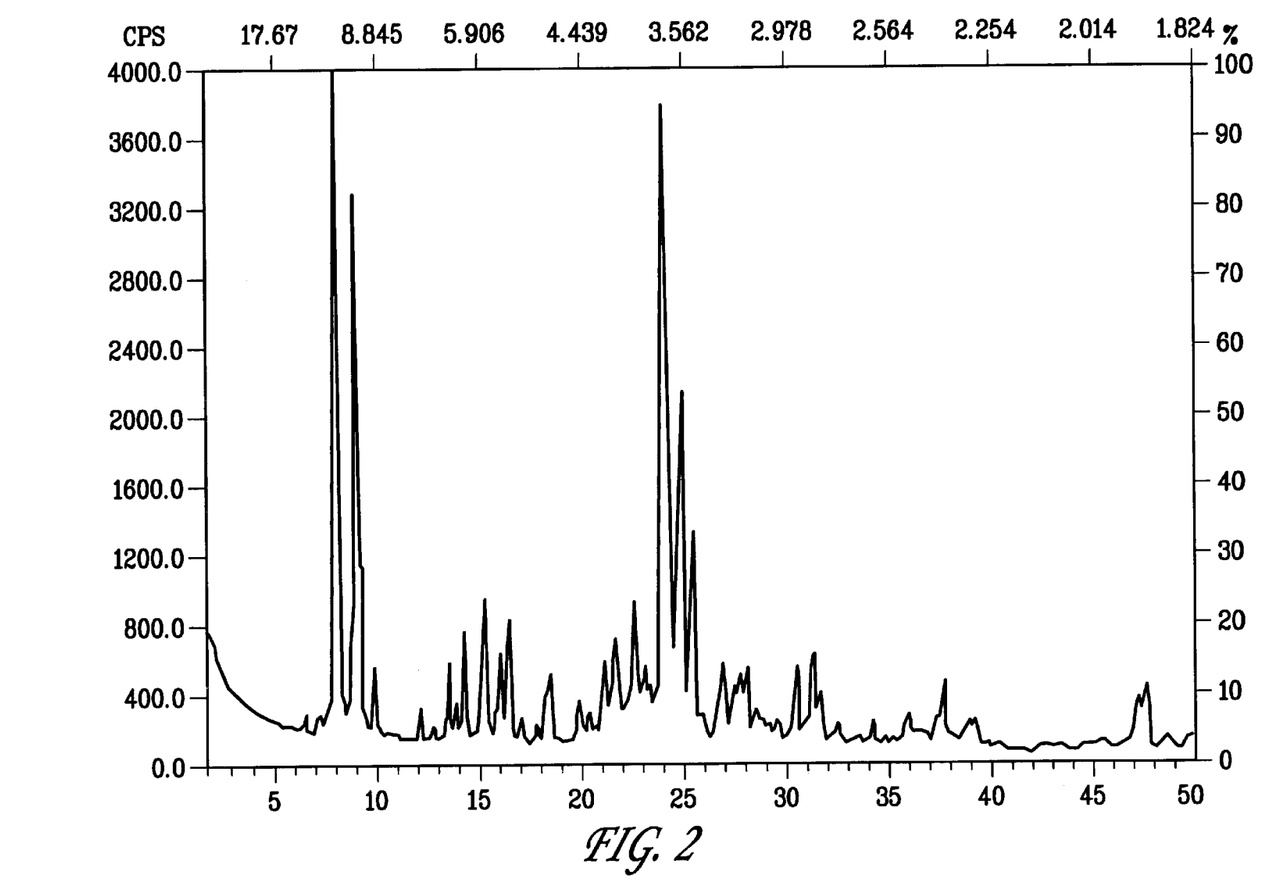
FIG. 2 is an x-ray diffraction pattern of the calcined ZSM-5 produced using N-cyclohexylglycine as the directing agent (Example 5).

An amount of 330.2 grams of the gel was transferred into a 600 ml Parr reaction. The reactor was closed and flushed with nitrogen. The mixture was heated to 165° C. under a nitrogen pressure of 400–450 psig with stirring. Approximately 2 hours after the temperature reached 165° C. the stirrer was stopped and the mixture was allowed to age statically for 24 hours. The stirrer was again turned on and the reaction was carried out at 165° C. for 11 days. Upon cooling the reactor was opened, and the solid product was separated by filtration. The crystalline product was washed with water, dried and then calcined at 538° C. for 10 hours in nitrogen followed by 10 hours in air. X-ray diffraction gave the pattern of FIG. 1 and showed that the product was ZSM-5 with high crystallinity. The $SiO_2/Al_2O_3$ molar ratio was analyzed to be 37.3 and the hydrogen form of the zeolite had an alpha value of 1454.

Figure 4A:
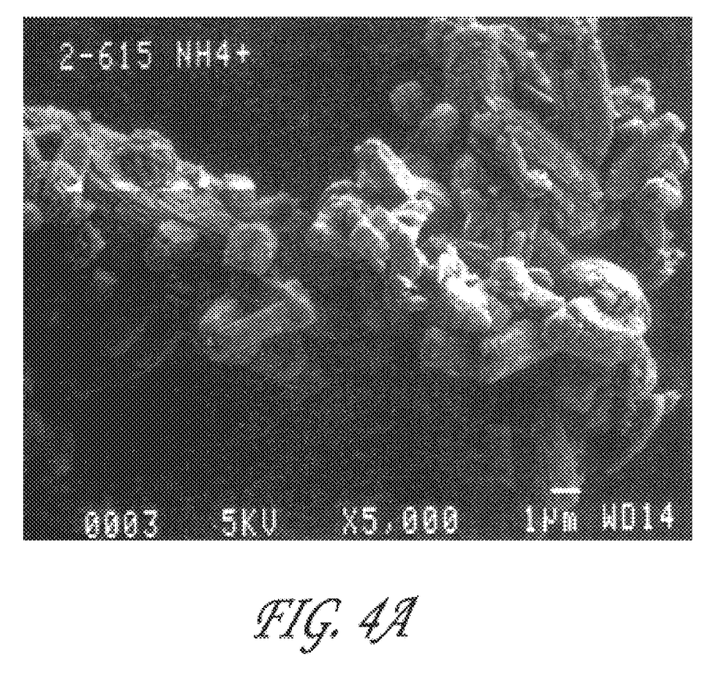
FIG. 4 is a SEM of the ZSM-5 synthesized with N-2-adamantylglycine in Example 2.
Figure 4B:
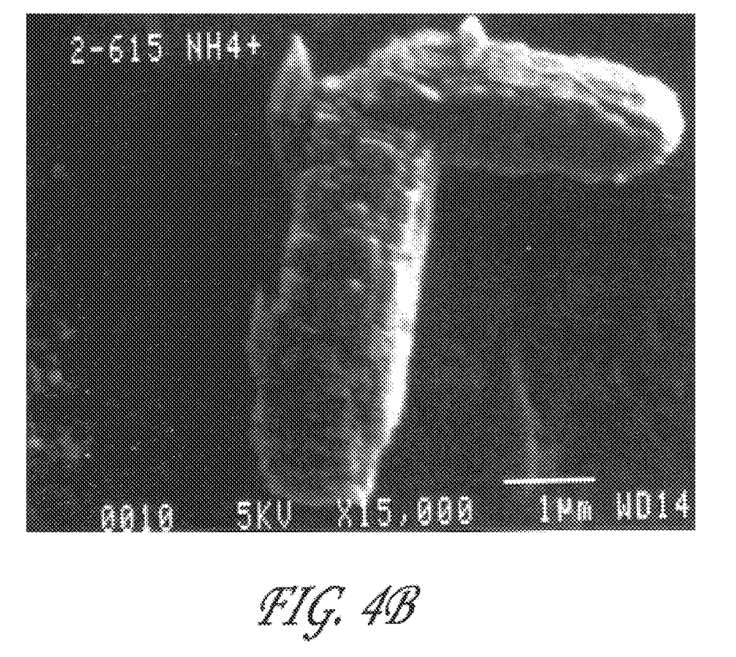

Scanning electron micrographs of the ammonium form of the product are given in FIG. 4 and indicate the crystal size to be in excess of 1 micron.

EXAMPLE 3

Synthesis of Cyclohexylglycine

Similar equipment and procedure as described in Example 1 were employed. 75.5 grams glycine (1.01 moles, Aldrich, 99+%), 118.4 grams cyclohexanone (1.21 moles, Aldrich 99.8%), 300 ml glacial acetic acid and 11.2 grams of Pd (5%)/C were used. The reaction was carried out in a 600 ml Parr reactor under 1000 psig (7000 kPa) hydrogen pressure at 75° C. No noticeable hydrogen uptake was noticed after 1.5 days, and the reaction was carried out for 4.5 days. The reactor was opened after cooling to room temperature. The solid catalyst was filtered by suction. The filtrate was evaporated to remove the acetic acid and the excess cyclohexanone. A viscous crude product (brown) remained which started to crystallize upon cooling to room temperature. The crude product was stirred into excess ether whereby a white solid precipitated out. The solid was filtered, washed with ether and dried. The solid was redissolved in a very small amount of acetic acid and recrystallized by adding an appropriate amount of ether. 144.5 grams of white crystals were recovered (91% yield based on glycine). Elemental analysis:calculated: C:61.12; H:9.62; N:8.91; 0:20.36; found:C:60.96; H:9.75; N:8.88; 0:20.41.

EXAMPLE 4

ZSM-5 Synthesis using N-Cyclohexylglycine

To 400 grams $NaAlO_2$/NaOH stock solution used in example 2 were added 11.5 grams N-cyclohexylglycine (0.073 moles). A clear solution was formed at room temperature. The solution was heated to 70–75EC before the addition of 86.4 grams of $SiO_2$ sol (30% $SiO_2$ in $H_2O$). A thin gel was formed:N-cyclohexylglycine/$SiO_2$=0.17; pH of gel=12.7. The gel was transferred into a 600 ml Parr reactor. The reactor was closed and purged with nitrogen. The reaction was heated to and stirred at 165° C. for an hour. The stirrer was stopped and the reaction was aged statically at 165° C. for 24 hours. The stirrer was restarted and the reaction was carried out at 165° C. for 7 days. The reactor was opened after cooling. The product was filtered, washed with water until the washing was neutral and dried at 110° C. under vacuum. The as synthesized zeolite was identified to be ZSM-5, with $SiO_2$/$Al_2O_3$=22.2.

Figure 5A:
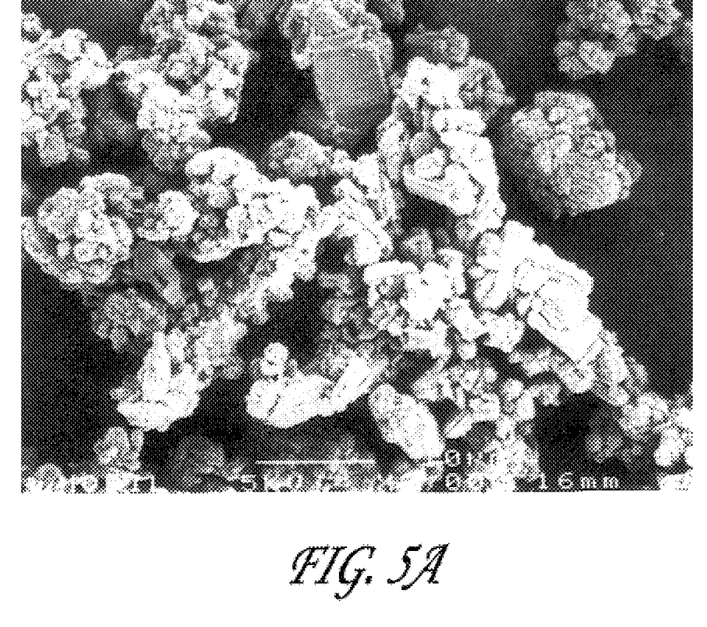
FIG. 5 is a SEM of the ZSM-5 synthesized with N-cyclohexylglycine in Example 4.
Figure 5B:
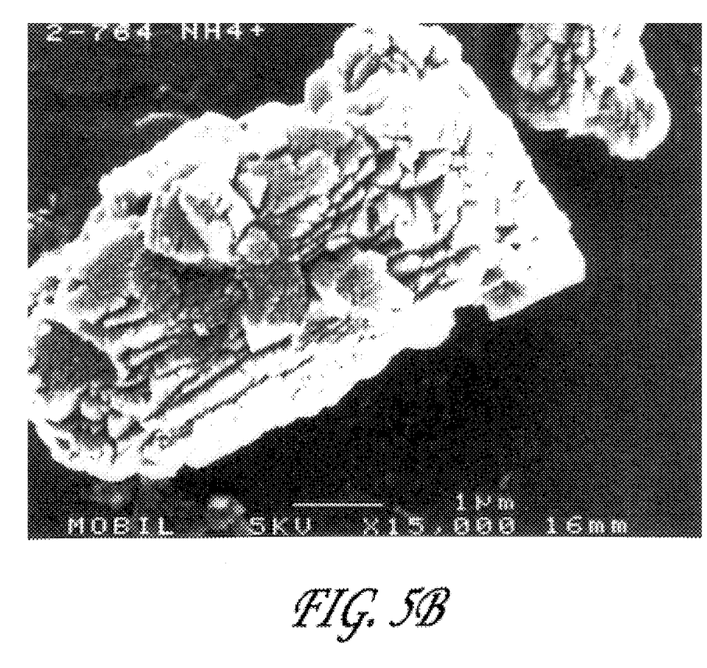

Scanning electron micrographs of the product are given in FIG. 5 and indicate the crystal size to be in excess of 1 micron.

EXAMPLE 5

ZSM-5 Synthesis Using 6-aminohexanoic Acid

Figure 6A:
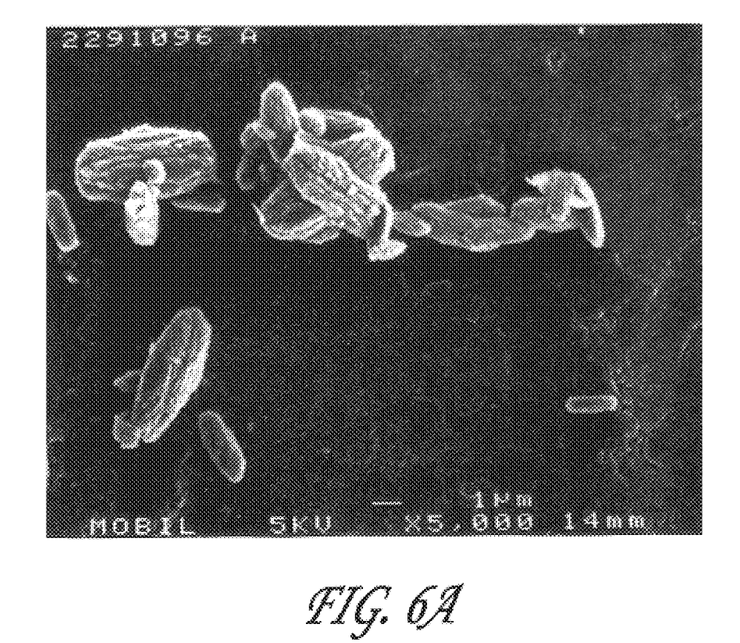
FIG. 6 is a SEM of the ZSM-5 synthesized with 6-aminohexanoic acid in Example 6.
Figure 6B:
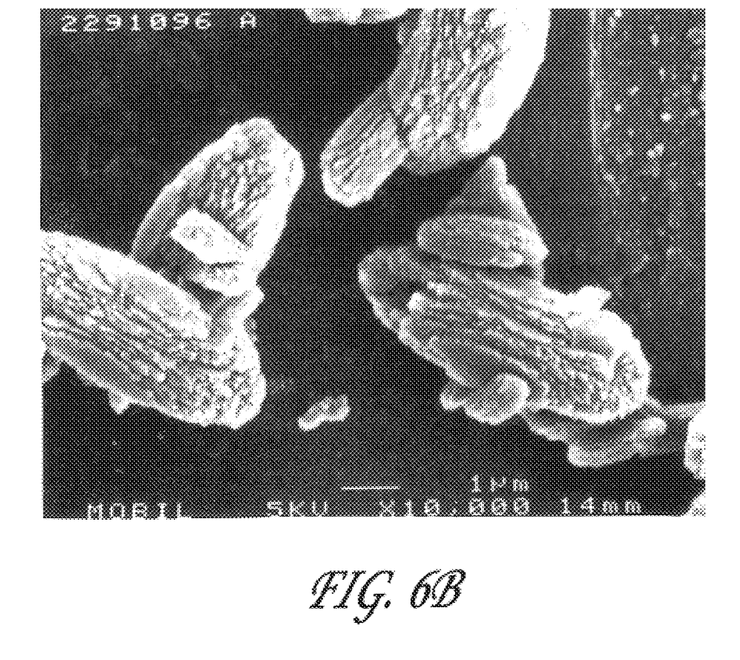

To 200 grams of $NaAlO_2$/NaOH stock solution of Example 2 were added 4.72 grams 6-aminohexanoic acid (Aldrich 98%, 0.036 moles). A clear solution was formed at room temperature. The mixture was heated to 70–75° C. and 43.21 grams of $SiO_2$ sol (30% $SiO_2$ in $H_2O$) were added to from a thin gel. The gel was transferred to a Parr reactor and heated at 165° C. with stirring. After 1 hour, the stirring was stopped and the mixture was aged statically at 165° C. for 24 hours. The stirring was restarted and the reaction was carried out at 165° C. for 8 days. A crystalline product identified by x-ray diffraction as ZSM-5 was obtained. Scanning electron photomicrographs (FIG. 6) showed that the ZSM-5 contained large crystals (>1 micron). Elemental analysis gave the $SiO_2$/$Al_2O_3$ as 25.8, whereas NMR determinations of framework Al and Si gave a $SiO_2$/$Al_2O_3$ ratio of 28.8. The alpha value of the zeolite in the hydrogen form was determined to be 998.

EXAMPLE 6

Example 5 was repeated with a reaction mixture having the following composition in molar ratios:

$SiO_2$/$Al_2O_3$=29.2

Na+/$SiO_2$=0.44

6-aminohexanoic acid/$SiO_2$=0.19

$H_2O$/$SiO_2$=64

Figure 3:
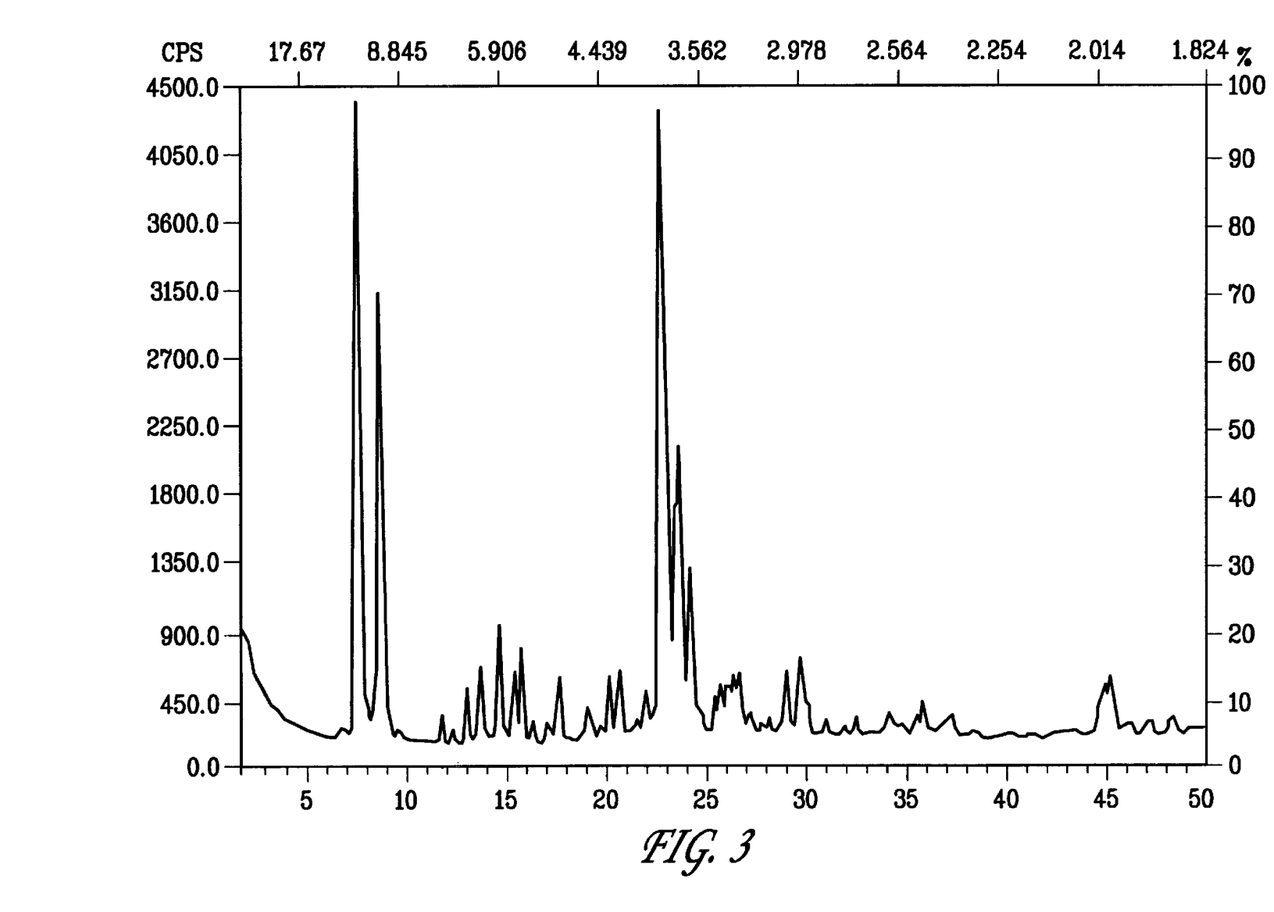
FIG. 3 is an x-ray diffraction pattern of the calcined ZSM-5 produced using 6-aminohexanoic acid as the directing agent (Example 6).

The water was charged into the one-gallon reactor. With stirring the NaOH was added. When a clear solution was formed, the $NaAlO_2$ was added. The mixture was stirred until complete dissolution. The solution was heated to 70–75° C. and the $SiO_2$ sol was added with stirring. A thin gel was formed. The reactor was closed and heated to 165° C. with stirring at 100 rpm. After stirring at 165° C. for 1.9 hours, the stirrer was turned off and the mixture was allowed to age statically for 24 hours. The stirrer was restarted and the reaction was carried out at 165° C. for 2 days. The reactor was opened after cooling to room temperature. The product was filtered by suction and washed to neutral pH with deionized water. The as-synthesized zeolite was dried. Five grams were calcined in air at 538° C. for 10 hours. The calcined zeolite was exchanged with 1 N $NH_4NO_3$ and recalcined in air to give the H+ form. X-ray diffraction (FIG. 3) showed that the product was ZSM-5 and SEM (FIG. 6) showed large crystals were formed. Elemental analysis revealed Si:35.57% and Al:3.09%, corresponding to a mole ratio of $SiO_2$/$Al_2O_3$ of 22.1. The alpha value was determined to be >1000. The Toluene Diproportionation Index (TDI) of the zeolite was measured to be 392.

EXAMPLE 7

Example 5 was repeated with a reaction mixture having the following composition in molar ratios:

$SiO_2$/$Al_2O_3$=26.1

Na+/$SiO_2$=0.50

6-aminohexanoic acid/$SiO_2$=0.31

$H_2O$/$SiO_2$=70.6

The $H_2O$ was added into a one-gallon Parr reactor. The NaOH, $NaAlO_2$, and the 6-aminohexanoic acid were successively dissolved into the $H_2O$. At room temperature and with stirring, the $SiO_2$ sol was added to the mixture and a thin gel was formed. The reactor was closed, pressurized with 148 psi nitrogen, and stirred at 100 rpm at room temperature for an hour. The stirrer was stopped and the mixture was aged statically at room temperature for 24 hours. The reaction mixture was heated to 185° C. with stirring at 100 rpm. After 24 hours, a sample was taken. X-ray diffraction showed that the product had started to crystallize. The reaction was terminated after 2 days. X-ray diffraction showed that the product was highly crystalline ZSM-5.

EXAMPLE 8

Example 7 was repeated without the static aging step and with the reaction mixture having the following molar ratios:

$SiO_2$/$Al_2O_3$=32.5

Na+/$SiO_2$=0.4

6-aminohexanoic acid/$SiO_2$=0.17

$H_2O$/$SiO_2$=58.3

After the reactor was closed, the reaction was carried out at 165° C. with stirring at 100 rpm for 5 days. The reactor was opened after cooling to room temperature. The product was filtered by suction and washed to neutral pH with deionized $H_2O$ and dried at 110° C. under vacuum. Five grams of the product were calcined, exchanged with 1 N $NH_4NO_3$ and calcined to give the H+ form. XRD showed that the product was ZSM-5 and SEM showed that large crystals were formed. The alpha value was >1000 and the TDI was 390.

The ZSM-5 product was determined by NMR to contain all tetrahedral framework aluminum. Elemental analysis of a dried sample showed Si:42.69 wt. % and Al:2.66 wt. %. Based on the elemental analysis the bulk framework $SiO_2$/$Al_2O_3$ ratio was calculated to be 30.8. The surface concentration of all elements of the same zeolite was determined by XPS analysis. Atomic concentration of Si and Al detected Si:25.3 and Al:1.7. The surface framework $SiO_2$/$Al_2O_3$ ratio was calculated to be 30.0.

Similarly, the bulk and surface framwork $SiO_2$/$Al_2O_3$ ratios of a conventionally prepared large crystal ZSM-5 were determined. A comparison of results between the conventionally prepared large crystal ZSM-5 and the large crystal ZSM-5 prepared according to this Example is shown below.

Comparison of Aluminum Distribution

| Large Crystal ZSM-5 | $SiO_2/Al_2O_3$ | |
| --- | --- | --- |
| | Bulk | Surface |
| Conventional (amine templated) | 70 | 51 |
| This invention (amino acid templated as in Ex. 8) | 30.8 | 30.0 |

These results clearly show that the framework $SiO_2/Al_2O_3$ ratio is significantly lower (>20%) at the surface for the conventionally prepared large crystal ZSM-5, but essentially the same for the large crystal ZSM-5 of Example 8. In other words, these two large crystal ZSM-5 zeolites differ in aluminum distribution. Aluminum concentration is significantly higher (~20%) at the surface of the conventional large crystal ZSM-5; but the concentration is essentially the same at the surface and in the bulk of the large crystal ZSM-5 of Example 8.

The TDI for the conventional large crystal ZSM-5 was determined to be 451 (compared with the value of 390 for the product of Example 8), whereas a conventional small crystal ZSM-5 (<0.05 micron crystal size) was found to have a TDI of 445.

EXAMPLE 9

A reaction mixture having the following molar ratios was prepared from the starting materials used in the previous examples:

$SiO_2/Al_2O_3=36$
$Na+/SiO_2=0.39$
6-aminohexanoic acid/$SiO_2=0.17$
$H_2O/SiO_2=58.6$ The water was added to a one-gallon Parr reactor. The NaOH was added with stirring until a clear solution was formed. The $NaAlO_2$ was added with stirring until it was all-dissolved. The $SiO_2$ sol was added to the mixture with vigorous stirring at room temperature. pH of the starting gel:13.0. The Parr reactor was closed and the reaction was heated to 165° C. and stirred at 100 RPM. After 2 days, a sample was taken through a dip tube. The liquid had a pH of 11.3; the solid was a highly crystalline ZSM-5. The reaction was terminated. The solid was washed until the washing was neutral and dried. Weight of product:154.7 grams.

EXAMPLE 10

Example 8 was repeated but at a lower water content in the reaction mixture, which had the following molar composition:

$SiO_2/Al_2O_3=32.3$
$Na/SiO_2=0.40$
6-aminohexanoic acid/$SiO_2=0.17$
$H_2O/SiO_2=29.2$
Highly crystalline ZSM-5 (large crystals) was obtained.

EXAMPLE 11

The same molar ratios of the reagents in the starting mixture and the same procedure as described in Example 10 except a lower reaction temperature of 130° C. were employed in this synthesis. The reaction was carried out for 11 days and large crystal ZSM-5 was obtained. Elemental analysis showed a $SiO_2/Al_2O_3$ ratio of 25.1.

EXAMPLE 12

In this example, a solid silica source, Ultrasil (containing 90% $SiO_2$ and 10% $H_2O$) was used and the reaction mixture had a high solids content:

$SiO_2/Al_2O_3=29.2$
$Na+/SiO_2=0.44$
6-aminohexanoic acid/$SiO_2=0.19$
$H_2O/SiO_2=24.1$ The water was charged into a one-gallon Parr reactor. The NaOH, $NaAlO_2$, 6-aminohexanoic acid were successively dissolved into the water with stirring. The solution was heated to 70–75° C. and the $SiO_2$ was added with stirring to form a gel. The reactor was closed and the reaction was carried out at 140° C. and 100 RPM for 4 days. The reactor was opened after cooling to room temperature. The product was filtered and washed to neutral pH with deionized water. Thirty grams of the product were calcined in air and exchanged with $NH_4NO_3$ and calcined to give the H+ form. The product was a large crystal ZSM-5 which had an alpha value in excess of 1600.

EXAMPLE 13

Example 12 was repeated but with the starting mixture having the following molar ratios:

$SiO_2/Al2O_3=32.5$
$Na+/SiO_2=0.40$
6-aminohexanoic acid/$SiO_2=0.17$
$H_2O/SiO_2=21.4$ The reaction was carried out at 150° C. for 3 days. The product was large crystal ZSM-5 and weighed 313.5 gms. The H+ form of the product had an alpha value in excess of 850 and a TDI of 387.

EXAMPLE 14

Example 12 was repeated but with the starting mixture having the following molar ratios:

$SiO_2/Al2O_3=29.2$
$Na+/SiO_2=0.40$
6-aminohexanoic acid/$SiO_2=0.19$
$H_2O/SiO_2=23.7$
Similar large crystal ZSM-5 was obtained.

EXAMPLE 15

The procedure of Example 9 was repeated with the directing agent being L-glutamic acid and the starting mixture having the following molar composition:

$SiO_2/Al_2O_3=33.7$
$Na+/SiO_2=0.386$
Glutamic acid/$SiO_2=0.16$
$H_2O/SiO_2=56.6$ The reagents were charged to a one-gallon Parr reactor. The reactor was closed and heated to 165° C. for 3 days. After cooling, the product was filtered and washed free of base. Part of the product was $NH_4^+$ exchanged and calcined to the $H^+$ form. SEM revealed that large crystals were obtained. X-ray diffraction showed that the zeolite was ZSM-5.

Elemental analysis of the HZSM-5 indicated a bulk silica/alumina molar ratio of 29.5, whereas XPS analysis indicated the surface silica/alumina molar ratio to be 33.8.

EXAMPLE 16

Example 12 was repeated (using Ultrasil as the silica source) but with the directing agent being L-lysine as supplied by Aldrich Chemical Company and with the starting mixture having the following molar composition:

$SiO_2/Al_2O_3=32.6$
$Na+/SiO_2=0.398$
$L\text{-lysine}/SiO_2=0.17$
$H_2O/SiO_2=57.6$ The reagents were charged to a one-gallon Parr reactor. The reactor was closed and heated to 165° C. for 3 days. The reaction was stopped and the reactor allowed to cool. The product was filtered, washed free of base and dried in a 110° C. oven. Part of the as-synthesized zeolite was $NH_4^+$ exchanged and air calcined to the $H^+$ form. Analysis showed the product to be ZSM-5 with a molar ratio of 31.4.

EXAMPLE 17

Example 16 was repeated with a higher concentration of silica such that the starting mixture had the following molar composition:

$SiO_2/Al_2O_3=32.5$
$Na+/SiO_2=0.40$
$L\text{-lysine}/SiO_2=0.17$
$H_2O/SiO_2=21.4$ The water was charged into a one-gallon Parr reactor. The NaOH, $NaAlO_2$ and L-lysine were successively dissolved in the reactor with stirring. The solution was heated to 70° C. and the solid Ultrasil was added with rigorous stirring. A thick gel was formed. The Parr reactor was closed. The reaction was heated to 150° C. with 100 RPM stirring and maintained at these conditions for 3 days. The product was filtered and washed with deionized water until the washing was neutral. The dried product weighed 144.9 gm. Part of the as-synthesized zeolite (5 gm) was $NH_4^+$ exchanged and calcined in air to the $H^+$ form. X-ray diffraction showed that the product was highly crystalline ZSM-5. SEM showed that the product contained large crystals.

EXAMPLE 18

Example 17 was repeated using L-glutamic acid as the directing agent and the molar ratios of the starting mixture as follows:

$SiO_2/Al_2O_3=32.5$
$Na/SiO_2=0.40$
$L\text{-glutamic acid}/SiO_2=0.17$
$H_2O/SiO_2=21.4$ The water was charged into a one-gallon Parr reactor. The NaOH, $NaAlO_2$ and L-glutamic acid were successively dissolved in the reactor with stirring. The solution was heated to 70° C. and the solid Ultrasil was added with rigorous stirring. A thick gel was formed. The Parr reactor was closed. The reaction was heated to 150° C. with 100 RPM stirring and maintained at these conditions for 3 days. The product was filtered and washed with deionized water until the washing was neutral. Five grams of the product was $NH_4^+$ exchanged and calcined to the $H^+$ form in air. X-ray diffraction showed that the product was highly crystalline ZSM-5. SEM showed that the product contained large crystals. The TDI of the product was 390.

EXAMPLE 19

1.0 part of $Al_2(SO_4)_3 \cdot xH_2O$ was dissolved in 8.0 parts of $H_2O$. To this solution was added 1.98 parts of 50% sodium hydroxide solution. A solution obtained by dissolving 1.12 parts of the mono sodium salt of glutamic acid (MSG) in 2.71 parts of $H_2O$ was added to the above solution. To this mixture was added 4.03 parts of Ultrasil precipitated silica. The slurry was thoroughly mixed and then 8.0 g of ZSM-5 seeds (solids basis) slurried in 2.28 parts of $H_2O$ was added to the mixture and the final slurry mixed for 30 minutes. The composition of the reaction mixture in mole ratios was:

$SiO_2/Al_2O_3=36.0$
$OH/SiO_2=0.24$
$Na+/SiO_2=0.50$
$R/SiO_2=0.10$
$H_2O/SiO_2=12.8$

The mixture was crystallized in a stainless steel reactor, with stirring, at 100 rpm, at 156° C. for 60 hrs.

Figure 7:
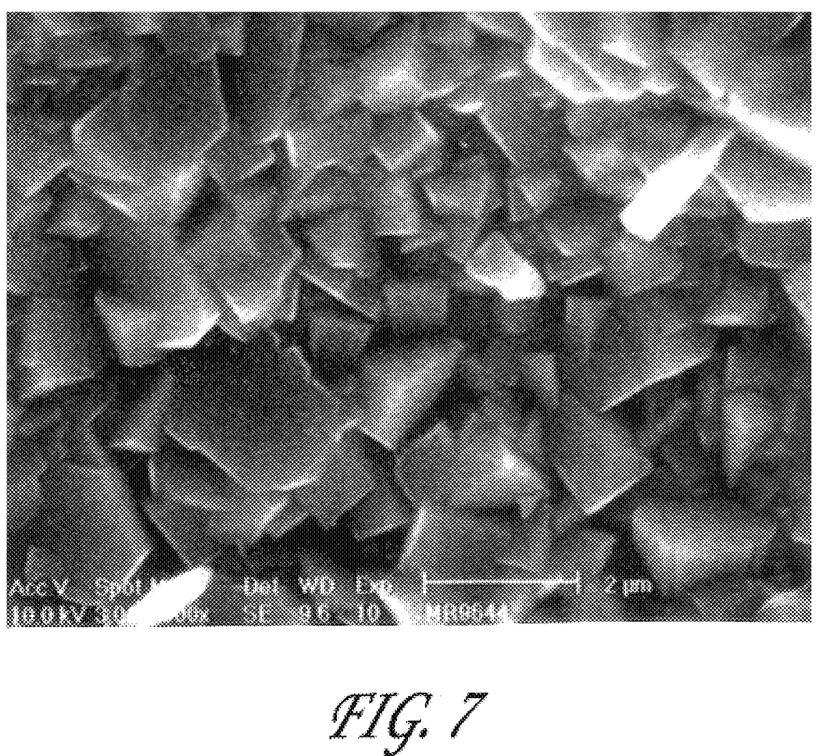
FIG. 7 is a SEM of the ZSM-5 synthesized with monosodium glutamate in Example 19.

The x-ray analysis of the product showed a crystalline ZSM-5 material. The bulk silica/alumina molar ratio of the material was 29.6. The product was calcined for 16 hrs. at 538° C. and the calcined material was contacted with 10% $NH_4Cl$ solution for three 1 hr contacts at 85° C., with stirring. The material was then calcined for 3 hrs. at 538EC to convert it to the hydrogen form. The material was found to have an alpha value of 1380 and a TDI of 390. SEM showed the presence of 1–3 micron crystals (FIG. 7). The material exhibited a sorption time for 2,2-dimethylbutane for 30% of its capacity, as measured at 120° C. and 60 torr (8 kPa) hydrocarbon pressure, of 11.6 minutes.

We claim:

1. A method of synthesizing a synthetic porous crystalline material having the structure of ZSM-5 and a composition involving the molar relationship:

$$X_2O_3:(n)YO_2,$$

wherein X is a trivalent element; Y is a tetravalent element; and n is greater than about 12, and wherein the crystals have a major dimension of at least about 0.5 micron, said method comprising the steps of forming a reaction mixture containing sources of an alkali or alkaline-earth metal oxide, a trivalent metal oxide $X_2O_3$, a tetravalent metal oxide $YO_2$, water, and an amino acid or salt thereof having the formula:

wherein $R_1$ is $NH_2$ or a carboxylic acid group or salt thereof; $R_2$ is alkyl, aryl, alkaryl, $NH_2$ or $NHR_3$ where $R_3$ is an adamantyl or cyclic alkyl group; A is H or a metal and z is from 0 to 15, provided that at least one of $R_1$ and $R_2$ is $NH_2$ or $NHR_3$, and crystallizing the reaction mixture to produce said porous crystalline material, wherein the surface $YO_2/X_2O_3$ ratio is no more than 20% greater than the bulk $YO_{02}/X_2O_3$ ratio of the crystal.

2. The method of claim 1 wherein z is from about 1 to about 7.

3. The method of claim 1 wherein the amino acid or salt thereof is selected from the group consisting of lysine, glutamic acid and monosodium glutamate.

4. The method of claim 1 wherein the amino acid or salt is glutamic acid or monosodium glutamate.

5. The method of claim 1 wherein the reaction mixture has the following composition in terms of mole ratios of oxides:

| | |
|---|---|
| $YO_2/X_2O_3$ | 20–80 |
| $H_2O/YO_2$ | 10–90 |
| $AA/YO_2$ | 0.05–0.5 |
| $M/YO_2$ | 0.1–0.8. |

6. The method of claim 1 wherein the reaction mixture has the following composition in terms of mole ratios of oxides:

| | |
|---|---|
| $YO_2/X_2O_3$ | 20–40 |
| $H_2O/YO_2$ | 20–60 |
| $AA/YO_2$ | 0.1–0.2 |
| $M/YO_2$ | 0.3–0.4. |

7. The method of claim 1, wherein X is selected from the group consisting of aluminum, boron, iron, gallium and mixtures thereof, and Y is selected from the group consisting of silicon, germanium and mixtures thereof.

8. The method of claim 1 wherein X is aluminum and Y is silicon.

9. The method of claim 1 wherein crystallization is effected at a temperature of 80 to 225° C.

10. The method of claim 1 wherein crystallization is effected at a temperature of 120 to 200° C.

* * * * *

UNITED STATES PATENT AND TRADEMARK OFFICE
CERTIFICATE OF CORRECTION

| | |
|---|---|
| PATENT NO. | : 6,013,239 |
| APPLICATION NO. | : 08/952030 |
| DATED | : January 11, 2000 |
| INVENTOR(S) | : Chen et al. |

It is certified that error appears in the above-identified patent and that said Letters Patent is hereby corrected as shown below:

Claim 1, col. 12, line 59, replace "greater" with --less--.

Signed and Sealed this

Eighth Day of August, 2006

JON W. DUDAS
*Director of the United States Patent and Trademark Office*